United States Patent [19]

Maronian

[11] Patent Number: 5,113,874

[45] Date of Patent: * May 19, 1992

[54] MEMBRANES USEFUL IN PREPARING PROPHYLACTIC DEVICES HAVING PATHOGEN RESISTANT BARRIERS, AND FLEXIBLE ELECTRODES

[75] Inventor: Hovaness H. Maronian, Rochester, N.Y.

[73] Assignee: Rochester Medical Devices, Inc., Rochester, N.Y.

[*] Notice: The portion of the term of this patent subsequent to Dec. 3, 2008 has been disclaimed.

[21] Appl. No.: 423,899

[22] Filed: Oct. 19, 1989

Related U.S. Application Data

[63] Continuation-in-part of Ser. No. 261,050, Oct. 21, 1988, abandoned.

[51] Int. Cl.⁵ ............................................. A71F 6/04
[52] U.S. Cl. ................................. 128/844; 604/347; 427/2
[58] Field of Search ............... 128/844, 635, 639, 784; 604/347-351; 427/2, 171; 204/192 C, 192 SP

[56] References Cited

U.S. PATENT DOCUMENTS

| | | |
|---|---|---|
| 1,580,857 | 4/1926 | Richards. |
| 1,801,722 | 4/1931 | Geer. |
| 2,278,722 | 4/1942 | Loiseleur. |
| 4,397,706 | 8/1983 | Allen et al. . |
| 4,407,871 | 10/1983 | Eisfeller. |
| 4,576,156 | 3/1986 | Dyck et al. . |
| 4,588,646 | 5/1986 | Athey, Jr. . |
| 4,653,499 | 3/1987 | Murray, Jr. et al. ............... 128/635 |
| 4,654,271 | 3/1987 | Mauer et al. . |
| 4,684,490 | 8/1987 | Taller et al. . |
| 4,737,188 | 4/1988 | Bahls . |
| 4,827,932 | 5/1989 | Ideker et al. ..................... 128/784 X |
| 4,923,469 | 5/1990 | Frachet et al. ............. 128/420.5 X |
| 4,935,260 | 6/1990 | Shlenker ......................... 128/844 X |
| 4,935,345 | 6/1990 | Guilbeau et al. ............... 128/635 X |
| 4,940,065 | 7/1990 | Tanagho et al. ..................... 128/784 |
| 4,959,130 | 9/1990 | Josowicz et al. ............... 128/635 X |
| 4,961,434 | 10/1990 | Stypulkowski ..................... 128/784 |

FOREIGN PATENT DOCUMENTS

| | | |
|---|---|---|
| 1566376 | 4/1970 | Fed. Rep. of Germany . |
| 1616474 | 4/1971 | Fed. Rep. of Germany . |
| 8800818 | 3/1990 | PCT Int'l Appl. . |
| 9002534 | 3/1990 | PCT Int'l Appl. ................. 128/844 |
| 927369 | 5/1963 | United Kingdom . |
| 1154571 | 6/1969 | United Kingdom . |
| 2065718 | 7/1981 | United Kingdom . |

Primary Examiner—Robert A. Hafer
Assistant Examiner—Kerry Owens
Attorney, Agent, or Firm—Birch, Stewart, Kolasch & Birch

[57] ABSTRACT

The disclosure relates to flexible membrane structures having a layer of a ductile metal thereon or sandwiched therein. The disclosure further relates to improved prophylactic devices having improved resistance to the transmission of very small viruses, such as AIDS or HERPES therethrough, which utilize the flexible membrane structures of the present invention, and the present invention furthermore relates to flexible electrodes which utilize the flexible membrane structures of the present invention. The present invention also relates to methods of making such membranes, electrodes, and prophylactic devices.

40 Claims, No Drawings

MEMBRANES USEFUL IN PREPARING PROPHYLACTIC DEVICES HAVING PATHOGEN RESISTANT BARRIERS, AND FLEXIBLE ELECTRODES

This application is a continuation-in-part of U.S. application Ser. No. 07/261,050, now abandoned, filed on Oct. 21, 1988, incorporated herein by reference.

FIELD OF THE INVENTION

The present invention relates to flexible membrane structures having a layer of a ductile metal thereon or sandwiched therein. The present invention further relates to improved prophylactic devices having improved resistance to the transmission of very small viruses, such as AIDS or HERPES therethrough, which utilize the flexible membrane structures of the present invention, and the present invention furthermore relates to flexible electrodes which utilize the flexible membrane structures of the present invention. The present invention also relates to methods of making such membrane electrodes and prophylactic devices.

BACKGROUND OF THE INVENTION

Prophylactic devices for the prevention of sexual disease, as used in large numbers throughout the world, are most often made of natural rubber latex material in very thin wall thicknesses ranging from 0.3 millimeters (30 micrometers) to 0.7 millimeters (70 micrometers). Such very thin membranes of highly elastic natural materials have been found most desirable to minimize interference with active movement during use as well as permitting the users to retain the nerve sensations and experiences during such use.

However, natural rubber material, in such thin wall membranes, does not provide a continuous, impermeable barrier to the passage of micro-size pathogens, such as the virus causing AIDS or HERPES. Such virus are known to be as small as 0.1 micrometer (0.001 millimeter), or about 250 times smaller than the length of the human sperm and at least 30 times smaller than the thickness of such sperm. The natural rubber membrane is comprised of a polymer matrix characterized by myriads of randomly distributed microsize openings or pores formed among polymer chains. Thus, although such natural rubber prophylactics have been found to be an effective barrier preventing the transmission of the larger sperm, there is no assurance that such devices are effective in preventing the transmission of such much smaller virus, and some testing to date has indicated to the contrary.

Additionally, the elastic membrane is usually cyclically stretched and relaxed in three dimensions during its intended use, resulting in repeated stressing of the membrane and reductions in its wall thickness, during such use. This action is believed to result in repeatedly enlarging and reducing the micro-size openings in the membrane, thereby increasing the probability of pathogens passing through the membrane.

Still further, despite extensive quality control testing of the prophylactics during manufacture, the membranes are not manufactured with absolutely uniform wall thicknesses, and therefore, during use different areas of the walls are not uniformly stressed nor uniformly stretched, resulting in "weaker spots" or areas and occasional bursting under severe stressing. The International Planned Parenthood Federation estimates that even from the best manufacturers, prophylactics have a bursting rate during use of 0.1% whereas those from the worst manufactured brands have a burst rate as high as 1%. Similar statistical data is not yet available, or has been published, with respect to the effectiveness of rubber prophylactics in preventing the transmission of virus, such as those causing AIDS and HERPES. It is widely believed, however, that presently available prophylactics are not very effective in preventing the transmission of such sexually transmitted diseases.

Before arriving at the present inventive prophylactics and methods, I first hypothesized that conventional prophylactics could be improved by providing a metal film or coating over the rubber membrane to effectively seal the micro-size openings therein, and therefore provide an improved barrier to the passage of such small virus. However, my tests showed that cyclically applied elastic stretching and relaxing of the coated rubber membrane, such as occurs during use, resulted in disrupting the metal layer, including the forming of cracks and fractures in the metal layer.

SUMMARY OF THE INVENTION

In view of the above drawbacks associated with prophylactic devices known in the art, there are provided for herein novel membrane type structures, which are applicable in the manufacture of improved prophylactic devices, which devices overcame drawbacks associated with the prior art. Fortuitously, it has also been discovered, and is provided for herein, that the novel membrane structures disclosed herein can be utilized advantageously to form flexible electrodes, which electrodes can be utilized in a wide array of situations.

Accordingly the present invention provides for the following:

1. A flexible membrane comprising:
   (a) a first continuous thin elastic membrane layer; and
   (b) a thin layer of a ductile metal, which is adjacent to and supported by said membrane layer;
   said membrane layer consisting of a material capable of stretching and relaxing without normally experiencing a permanent set or fracturing or tearing of the membrane layer, and said membrane layer consisting of a matrix having submicroscopically small pores formed therein during manufacture, with said pores tending to enlarge during stretching of the membrane and to contract during relaxation of the membrane from a stretched state;
   said ductile metal layer having an undulating appearing surface when the membrane is in a relaxed state, and said undulating surface being extended and progressively smoothened as the membrane layer is elastically expanded, without breaking or fracturing of the ductile metal layer.

2. The flexible membrane of paragraph 1, further comprising a second thin continuous elastic membrane layer adjacent to said metal ductile layer;
   said second membrane layer consisting of a material capable of stretching and relaxing without normally experiencing a permanent set or fracturing or tearing of the membrane layer, and said second layer consisting of a matrix having submicroscopically small pores formed therein during manufacture, with said pores tending to enlarge during stretching of the membrane, and to contract during relaxation of the membrane from a stretched state._

3. The flexible membrane of paragraph 1, further comprising a second thin continuous elastic membrane layer adjacent to said first thin continuous elastic membrane;

said second thin elastic membrane layer being characterized as in paragraph 2, above.

4. The flexible membrane of paragraph 2 or 3, further comprising a third thin elastic membrane layer adjacent to said first or second of said thin continuous membrane layers;

said third thin elastic membrane layer consisting of a material capable of stretching and relaxing without normally experiencing a permanent set or fracturing or tearing of the membrane layer, and said third membrane layer consisting of a matrix having sub-microscopically small pores formed therein during manufacture, with said pores tending to enlarge during stretching of the membrane and to contract during relaxation of the membrane.

5. An improved prophylactic device having an improved barrier to resist the transmission of sexually transmitted viruses, including those viruses causing AIDS or HERPES, which device comprises:

one of the flexible membranes disclosed in paragraphs 1 and 4 above.

6. A flexible electrode, comprising:

one of the flexible membranes disclosed in paragraphs 1 to 4 above, with the proviso that at least a portion of said ductile metal layer is exposed.

7. A flexible electrode, comprising:

(a) one of the flexible membranes disclosed in paragraphs 1 to 4 above, with the proviso that at least a portion of said ductile metal layer is exposed; and (b) an electrical contact lead, which is in contact with said ductile metal layer.

DETAILED DESCRIPTION OF THE INVENTION

The flexible membrane structures provided for herein are, as noted, useful in preparing improved prophylactic devices as well as flexible electrodes. As such in the description which follows, many aspects of the present invention are discussed in relation to improved prophylactic devices made with membranes encompassed herein, as well as the flexible electrodes prepared with the membranes encompassed herein. Additionally, it is noted that many of the aspects of the present invention, which relate to the preparation of prophylactic devices and electrodes, herein encompassed, are generally applicable to the membrane structures, herein encompassed, no matter if a membrane structure herein encompassed is not utilized to prepare a prophylactic device or a flexible electrode.

The above considerations should be understood to apply when reviewing the following section on prophylactic devices, as well as the section thereafter on flexible electrodes and the Examples contained herein. Moreover, one should understand that the following discussions are primarily meant to teach those of ordinary skill in the art, how to practice the present invention, which of course, includes preparing membranes, prophylactic devices and electrodes herein encompassed, and that the same discussion should not be construed to limit the present invention, since only the claims appended hereto limit the present invention.

PROPHYLACTIC DEVICES

In the present invention it has been found that a substantially continuous thin, ductile metal coating or layer may be provided over the surface of the prophylactic device, without fracture or breaking despite repeated stretching and relaxing of the device such as would occur during intended use. This is accomplished by forming the metal layer in such fashion that it can be repeatedly expanded and contracted, with the elastic membrane, without fracturing or breaking of the thin metal layer. According to one preferred manufacturing process, the elastic membrane is initially stretched to the extent of its intended use, and a continuous coating of highly ductile metal is thinly applied to the stretched membrane to seal its surface. In another process, the stretched membrane is initially thinly coated with an additional elastic material, same or different, and the resulting coated device permitted to again relax, forming a pattern of wrinkles on its surface. The thin ductile metal seal is thereafter applied to the wrinkled surface, without or with stretching, thereby to form a correspondingly wrinkled metal layer that can be expanded and contracted without fracture or breaking. In still a third process, the surface of the membrane is prepared in a similar configuration of undulations or wrinkles, and is then continuously coated with a thin layer of highly ductile metal, thereby to provide an expandable metal seal. In what may be considered a fourth process, a membrane formed by any of the above processes, can additionally have applied thereto, adjacent to at least a portion of the exposed surface of a thin ductile metal layer, or thin elastic layer, additional thin elastic material layers.

In the present invention, it has been found that microsize openings that are formed in conventionally manufactured prophylactic articles, of natural latex rubber or other such elastic materials, can be sealed by a continuous, thin film, coating, or layer of a ductile metal, such as aluminum; and that such a seal can be maintained despite repeated stretching and relaxing of the elastic article without fracturing or cracking the thin metal layer. This is performed by using a highly ductile metal for the layer and by forming the layer with undulations, folds, or wrinkles in its thickness, such that the metal layer can be expanded and contracted to progressively smoothen the folds and restore the folds, without fracture or breaking of the metal seal.

In one preferred process of manufacture, a conventional prophylactic article comprising a latex rubber layer adjacent to a silicon rubber layer is prestretched on a mold to the extent expected during use, and is coated with substantially pure aluminum, in a vacuum deposition chamber, to form a thin, continuous film of aluminum directly onto the silicon rubber surface of the latex/silicon rubber article. The coating process is continued to form a metal film having a thickness ranging from 500 Angstroms to 5,000 Angstroms, preferably 1,000 to 5,000 Angstroms.

In the above latex/silicon rubber device, it is thought preferable to coat the metal ductile layer on the silicon rubber layer and not the latex rubber layer, since it is thought that the thin ductile metal layer generally adheres better to silicone rubber than late rubber. To insure that a deposited metal layer properly adheres to the stretched silicon rubber surface, referred to above, the surface is preferably carefully cleaned by chemical solvents, and/or by other cleaning methods prior to metalizing of the surface.

Upon completion of the metal coating process, the metalized article is removed from the vacuum chamber, and from its expansion mold, and permitted to relax, if previously stretched, to the normal relaxed size of the article.

It is noted that when utilizing a method for preparing a prophylactic device herein, wherein a first thin continuous layer of an elastic material is stretched, and then applied thereto a second thin continuous layer of an elastic material, same or different from the first elastic layer, upon relaxing of the elastic membrane micro wrinkles or undulations are formed on the exterior surfaces of the elastic layers, as the result of a stressed interface existing between the two adjacent elastic layers. In such an instance, a thin ductile metal layer can be coated upon one of the exterior surfaces of the elastic layers, without stretching the elastic membrane, before applying the metal layer thereto. This is of course true, inasmuch as microwrinkles and/or undulations undulations already exist in the substrate to be coated.

If one desires to produce a prophylactic device with one of the membranes herein encompassed, wherein two adjacent layers of thin continuous elastic materials exists on at least one side (above or below), a thin ductile metal layer (as when a prophylactic device is prepared utilizing a membrane structure as recited in the paragraphs numbered 3 and 4 above), it is possible to form a stressed interface between adjacent elastic layers and the same is considered encompassed herein. Additionally, if desired, a stressed interface also can be formed between two elastic layer surfaces having a ductile metal layer disposed therebetween (a sandwich configuration), it is thought, that such a stressed interface produces advantageous membranes, prophylactic devices and flexible electrodes, all herein encompassed, since having a stressed interface at the position of the ductile metal layer, ensures the thin metal layer will have microwrinkles or undulation therein, so that the layer can be stretched without cracking or breaking.

A number of ductile metals may be used to provide the very thin metal seal in the membranes, prophylactic devices and flexible electrodes herein encompassed. Such ductile metals would include aluminum, gold, silver, platinum, and other metals, including metal alloys. All of these very ductile metals can be applied in very thin coatings to the elastomeric surface of the article by a vacuum vaporization process, as described in examples below, or by other known processes for coating metals, including metal sputtering and electroless plating. Such other plating methods may be more useful where the article is made from other substrate materials, other than natural latex rubber or silicon rubber, where such other materials cannot be plated by metal vaporization.

If desired, the thin ductile metal layer may be provided by plating a series of ductile metal films to the surface, instead of a single coating. Each of the different layers may be of the same metal, or of different ductile metals, and with each layer being applied successively over the previous layer.

It has been found that a minimum thickness of the metal must be coated to insure obtaining a continuous metal sealing of the surface of the article. This minimum thickness of the metal film depends upon a number of parameters, including the ductile metal being used, the process of forming the metal film, and the substrate material used in the prophylactic article.

Although natural rubber latex at present is the most widely used material for prophylactic devices, a number of other elastomeric materials are in lesser use, including silicon rubber, polyurethane, and acrylic resins. Generally any of these elastomeric materials can be considered as appropriate to utilize in preparing membranes herein encompassed.

As stated herein earlier, it is thought that since ductile metal layers appear to adhere to silicon rubber better than natural latex rubber, one may advantageously prepare a prophylactic device having two adjacent layers of elastomeric materials, one natural latex rubber, and one silicon rubber, with a ductile metal layer coated on the silicon layer. It has also been found that the plated thickness of this metal film can exceed the minimum thickness herein provided by about one order of magnitude, as shown by the Example 6 below, without impairing the performance of the metal seal or barrier, despite repeated stretching and relaxing of the article.

For the purpose of protecting the thin metal layer against abrasion, a thin film of a suitable lubricant, such as silicone oil, may be later applied over the metal coating. Alternatively, the metal film can advantageously be overcoated with a thin layer of an elastomeric material, such as provided for in the membranes herein encompassed. In the instance where the metal ductile layer has been applied to an elastical material substrate, which is in a stretched configuration, a protective elastic overlayer is applied over the ductile metal layer preferably while the article is in a stretched state. In this manner, the elastomeric overlayer conforms to undulations, wrinkles, and folds in the ductile metal layer that are formed when the article is relaxed.

A number of alternative general processes for making the membranes, prophylactic devices, and even flexible electrodes of the present invention may be used, some of which are exemplified in Examples contained herein.

In one process of the present invention, a prophylactic article can be prepared as in Example 1 below, wherein the elastic layer of the article in manufacture was prestretched and directly coated with a thin ductile metal layer.

In another process, the prophylactic article may be prestretched, as in Example 1 below to an extent expected during use, but then instead of directly coating with a ductile metal layer, the expanded article can be precoated with a thin continuous intermediate layer of an elastomeric material, such as natural latex rubber or silicon rubber. This precoating of the stretched article with an intermediate elastomeric layer may be performed by dip-coating, as is usually used in the manufacture of such articles. When such a procedure is utilized, there is formed a stretched interface between the two layers of elastomeric materials.

After such a precoating, the article can be removed from its stretching mold and permitted to elastically contract to its relaxed state. The shrinking of the article correspondingly shrinks the intermediate elastomeric layer, producing undulations, wrinkles, and folds in the surface of the intermediate layer as the article is relaxed. The wrinkled intermediate layer is then metalized or coated with a thin layer of aluminum, or other ductile metal, to provide a continuous metal covering and seal, covering the undulations, wrinkles, and folds in the intermediate layer.

In the same manner as discussed above, the resulting metalized article can be repeatedly stretched and relaxed, within the limit of the original stretching, without fracture, cracking, or breaking of the metal sealing film. Stretching of the article tends to progressively smooth undulations, folds, and wrinkles in both the intermediate elastomeric layer and in the correspondingly undulated metal layer, without destroying the integrity of the metal seal or barrier.

According to a still further process of making an improved prophylactic article, the outer surface of the elastomeric article is molded to provide undulations, wrinkles, or folds in its outer surface, thereby increasing its surface area. After molding, the surface is coated with a thin ductile metal layer, preferably while in a stretched state, so as to ensure that the metal layer coats all portions of the undulated surface; but even so, one may also coat a device while in a relaxed state, and the same is provided for in Example 7 below, the device coated is a flexible electrode.

It is also thought there can possibly be formed undulations, wrinkles or folds in an elastic layer by surface abrasion, or by chemical treatment of an elastomeric layer's surface. Such methods of surface preparation could be performed while the article is disposed on a mold and stretched or maintained in its relaxed state. Afterwards, a thin coating or film of ductile metal, such as aluminum, is then applied over the undulated surface, following and sealing the undulations, folds, and wrinkles in a continuous covering.

In all of the processes herein disclosed, ductile metal layers can generally be applied by vapor deposition under a vacuum, or by metal sputtering, or electroless deposition, and the resulting metalized article can be repeatedly stretched and relaxed without fracture, cracking, or breaking of the thin ductile metal layer.

It will be appreciated by those skilled in the art, that the size and number of the indulations, wrinkles, and folds formed in the ductile layers of the membranes, prophylactic devices and flexible electrodes herein encompassed determines the extent to which ductile metal layer can be expanded while maintaining its structural integrity.

It is further noted, that in many of the processes described above and the Examples below, the elastomeric prophylactic article is disclosed, or may be assumed, to be worked upon while in a conventional tubular shape, and manufacturing by conventional processes, such as dip-coating of the mold in liquid rubber latex material. Furthermore, the metalizing is disclosed in Examples below to be performed by vacuum deposition, or other coating process while this tubular article is supported on a mold. Even so, the present invention should not be considered limited by such disclosure, since it is known in the art to manufacture prophylactic articles from a flat elastomer sheet, by vacuum forming or blow molding the rubber sheet, as described in U.S. Pat. No. 4,576,156. Accordingly, in the present invention, the processes herein taught, including metalizing processes described above, should be considered as applicable to an elastomeric material in sheet form, prior to the vacuum forming or blow molding of the sheet into a tubularly shaped prophylactic article. Additionally, it is generally thought that membranes herein taught could be applicable in preparing a wide variety of prophylactic articles having various shapes, such as might conform to different body parts, by vacuum molding or blow molding a membrane sheet into the shape of a prophylactic device.

FLEXIBLE ELECTRODES

Many aspects of the present invention which relate to the production of flexible electrodes, are identical to those referred to in the above section on PROPHYLACTIC DEVICES, and therefore it is thought advantageous to consider the present section in conjunction with the above section.

One can generally assume that any membranes provided herein which would be useful in preparing a prophylactic device herein encompassed, is useful in preparing a flexible electrode herein encompassed. However, unlike the prophylactic devices herein taught, a flexible electrode encompassed herein, must have at least one portion of its ductile metal layer exposed, so an electrical current can flow from or to such metal layer. Furthermore, unlike the prophylactic devices herein taught, advantageously some of the flexible electrodes encompassed herein possess an electrical contact lead connected to the thin ductile metal layer of the flexible electrode, to aid in carrying an electrical charge or pulse to or from an exposed portion of the thin ductile metal layer. Such a lead, can advantageously be utilized for connecting the electrode to an electrical device or simply to an electrical circuit. An electrical contact lead, if present, it is generally thought should be insulated with a rubber elastomeric material. It is noted that the electrodes herein taught can advantageously be insulated by the elastomeric layers therein continued.

In Example 7 that follows, there is provided for a tri-layered pair of flexible electrodes in the shape of surgical gloves, which have electrical contact leads connected thereto. The same Example, however, should by no means be considered to limit the present invention to only this configuration of a flexible electrode, or even to an electrode only having a single layer of an elastic material on either side of a thin ductile metal layer.

Likewise, while a flexible electrode which is prepared by the procedure in Example 7, is formed on a mold having undulations thereon, any of the process provided for herein for preparing a membrane or prophylactic device herein encompassed, could be applicable to producing flexible electrodes, so long as the produced electrode has a portion of the thin ductile metal layer therein contained exposed for contact with any desired surface.

Of the flexible electrodes herein encompassed, those having a ductile metal layer which comprises a ductile noble metal (e.g. gold, silver or platinum) are preferred, since such ductile noble metals are relatively unsusceptible to oxidation.

Furthermore, while the procedure used to prepare the flexible electrode of Example 7 is thought advantageous to utilize herein, it is generally thought most preferable to prepare a flexible electrode with a process similar to that provided for preparing the prophylactic device of Example 1 below, wherein elastomeric layer(s) are stretched prior to metallizing. Likewise, additionally elastic coating layers could advantageously be applied to a portion of the metallized surface while it is in a stretched state. In such a manner, upon relaxation from its stretched state, a flexible electrode would be formed.

In the flexible electrodes, herein encompassed, the most advantageous to use are thought to be those that are fully insulated, except for the portions of the thin metal ductile layer contained therein, which are desired to be exposed, and, of course, at least one portion of an electrical contact lead, if the same is present. The electrodes herein encompassed can be insulated by the thin continuous layers of the elastomeric materials herein taught, such as natural latex rubber or silicon rubber. If desired, one might, of course, also use other insulating materials so long as the electrode remains flexible and the integrity of the ductile metal layer is not injured, and is capable of stretching without breaking or cracking.

The following Examples are meant to provide additional information to those studying the present invention, so that the same can be easily practiced. Examples 1-6 relate to the preparation of prophylactic devices with some of the membranes herein encompassed. Example 7 is related to preparing a flexible electrode with one of the membranes herein encompassed. These Examples should not be construed to limit the present invention, since all of the membranes herein encompassed can be used to prepare both prophylactic devices and flexible electrodes.

EXAMPLE 1

A prophylactic article of standard commercial manufacture was stretched in a mold in two dimensions to twice its normal length and thickness (100%). Its outside surface was then cleaned of contaminants by being swabbed with isopropyl alcohol. The mold was then placed in a CVC thermal evaporator of conventional commercial design, and vacuum metalized at a vacuum of about $10^{-4}$ TORR. The ductile metal used for coating was 99.7% pure aluminum, and this metal was resistance fired in the evaporator for a period of about (7) seven seconds. To obtain a more uniform coating on the article, the mold was supported on a revolving rack "cluster" inside of the evaporator, and revolved about five (5) times during a seven (7) second coating interval.

After metalized coating, the article was removed from the evaporator, and from its expansion mold, and permitted to resume its relaxed elastic state. It was then subjected to various tests, including an electrical conductivity test, and various observation tests under a 50 power microscope. These tests initially confirmed the continuity of the metal film over the article. The coated article was then subjected to repeated cycles of stretching and relaxation, within the 100% limit of its coating, while under microscopic examination. These tests revealed the undulated, wrinkled, or folded, surface configuration of the metal layer when the article was disposed in a relaxed state, and the progressive smoothing of the metal undulations, wrinkles, and folds as the elastic article was stretched. No fracturing, cracking, or breaking of the aluminum film was observed under the microscope during the repeated cyclical stretching and relaxing of the elastic article. The electrical conductivity tests also did not reveal any breaks in the electrical conductivity of the aluminum film during the repeated stretching and relaxing of the article.

EXAMPLE 2

A prophylactic article of standard commercial manufacture was stretched on a mold in three dimensions to one half greater (50%) than its normal length and diameter, and aluminum metalized in a vacuum evaporator in the same manner as in Example 1, above.

The same tests, as in Example 1, were conducted, but the cyclically repeated stretching and relaxing of the metalized article were limited to an extent only 50% greater than the relaxed length and diameter of the article. The test results were the same as found in Example 1.

EXAMPLE 3

The same process as in Examples 1 and 2 was conducted but the prophylactic was prestretched only 10% greater in size than in its relaxed state.

The resulting article was tested in the same manner as in Examples 1 and 2, but was stretched during testing by only up to 10% greater than in its relaxed state.

The test results were the same as found in Examples 1 and 2.

EXAMPLE 4

The same metalizing process, of Examples 1, 2, and 3 above, was performed using a standard, commercially available prophylactic article, but the elastic article was not prestretched during the metalizing of its surface with aluminum. Instead, the article was placed on a non-expansion mold and accordingly metal coated while in its relaxed state.

The resulting product was tested in the same manner as in Examples 1, 2, and 3 above; including cyclically stretching and relaxing the article while microscopically observing the metal surface, and electrically testing the metal surface.

The stretching of this article produced fractures, cracks, and crazing in the metal film layer that were observable under the microscope.

EXAMPLE 5

The metallized article samples in Examples 1, 2, and 3 were each subjected to additional cycles of repeated stretching and relaxing, but were expanded during stretching to a degree beyond the limit of their prestretching during the metalizing processes.

In all examples, when the articles were expanded beyond their prestretched limits during coating, the test revealed fracturing, cracking, and crazing of the aluminum film.

More specifically:

For the samples of Example 1: Cracks were found when expanded beyond 100% of the articles relaxed size.

For the samples of Example 2: Cracks were found when expanded beyond 50%.

For the samples of Example 3: Cracks were found when expanded beyond 10%.

For the samples of Example 4: Cracks were found for any expansion.

EXAMPLE 6

A series of additional prophylactic articles of standard commercial manufacture were metalized with aluminum using the same process as described above in Examples 1, 2, and 3. However, the aluminum layers were
coated to over twice the thickness as in Examples 1-5 (e.g. 1000 Angstroms to 5,000 Angstroms).

Each of these metalized articles were tested in the same manner as the corresponding one in the above Examples. The test results were found to be the same for the thicker aluminum films or layers than for the thinner aluminum layers.

EXAMPLE 7

Flexible Electrodes having a configuration similar to Surgical Gloves

Structural forms for molding human gloves, having numerous large undulations theron, are obtained The molds are dipped into a solution or mixture of liquid silicon rubber. The molds are removed from the solution of the elastomeric material, and on the glove molds solidifies a thin continuous layer of silicon rubber having undulations formed thereon. Next, the thin continuous layer of silicon rubber formed on the molds is swabbed clean with isopropyl alcohol, or a similar chemical cleaning agent.

After cleaning of the thin continuous layer of silicon rubber, the forms with the silicon rubber layer thereon are placed in a CVC thermal evaporator of commercial design, and the silicon rubber is vacuum metalized at a vacuum of about $10^{-4}$ TORR with at least 99% pure aluminum and is then resistance fired for about at least 7 seconds, while being rotated at about 1 revolution per second on a revolving platform. There is thus obtained an undulated metal layer on the silicon rubber, which conforms to the undulations of the silicon rubber layer thereon. After metalizing, the form with metalized silicon rubber layers thereon is removed from the thermal evaporator and an electrical contact lead copper wire is connected to the metalized layer on each glove, by means of a liquid solder, or other equivalent means such as a conductive adhesive, at about the wrist area of each glove. After connecting on the electrical lead to each of the gloves, the metalized gloves, still on the above forms, are again dipped into a liquid solution of silicon rubber, but not dipped so that all portions of the metal layer or electrical lead connected thereto are covered with silicon rubber. Specifically, a portion on the tip of one of the fingers, or thumb, of each glove, and a central portion (about half way between the gloves) of the electrical contact lead is not coated with silicon rubber. After this dip-coating of the gloves and electrical lead, the newly coated layer of silicon rubber on the gloves is allowed to solidify into a thin continuous layer of silicon rubber, having undulations thereon, which conform to undulations in the ductile metal layer. Thereafter, the so-formed gloves are removed from the forms on which they are situated, and the electrical lead is cut where it is not coated with a layer of silicon rubber, about half way between the gloves to provide two separate flexible electrodes in the shape of human gloves; the so-formed electrodes having an undular surface, and having on at least a portion of the tip of a finger, or thumb thereof, an exposed thin ductile layer of aluminum metal. The so produced electrodes are flexible, and the undulations formed in the electrodes allow for stretching of the electrodes without interfering with the integrity of the aluminum layer sandwiched between the two silicon rubber layers.

The present invention is only to be limited by the scope of the appended claims.

What is claimed is:

1. A prophylactic device having an improved barrier to resist the transmission of sexually transmitted virus, including those causing AIDS and HERPES comprising:
   a hollow article having a continuous thin elastic membrane wall that is preshaped to anatomically conform to portions of the body and provide a physical barrier which resists the transmission of pathogens,
   said membrane wall comprising a material, which is capable of cyclical elastic stretching and relaxing without normally experiencing a permanent set or fracturing or tearing of the membrane,
   said material consisting essentially of a matrix having submicroscopically small pores formed therein during manufacture, with said pores tending to enlarge during stretching of the membrane and to contract during relaxation of the membrane from its stretched condition,
   a thin layer of ductile metal on an outer surface of the membrane for sealing the pores therein,
   said thin ductile metal layer comprising a continuous vacuum deposited vapor of a ductile metal applied directly to the surface of the membrane, and
   said ductile metal layer having an undulated or wrinkled appearance when the membrane is in a relaxed state, and the undulated or wrinkled appearance being extended and progressively smoothed out as the membrane is elastically expanded, without breaking or fracturing of the metal layer,
   whereby said metal layer improves the barrier resistance of the prophylactic member to the passage of pathogens therethrough, despite cyclically repeated elastic stretching and relaxing of the membrane.

2. A prophylactic device having improved barrier resistance to the passage of pathogens, including the virus causing AIDS comprising:
   a thin elastic membrane that is normally capable of cyclically repeated stretching and relaxing while retaining its structural integrity,
   said membrane having plural microsized openings formed therein during manufacture that are subject to enlargement when the membrane is elastically stretched, and said membrane comprising a member selected from the group of natural latex rubber, silicone rubber, polyurethane, and an elastomeric acrylic resin,
   a thin ductile metal coating continuously covering the membrane for sealing the membrane to prevent the passage of pathogens through the microsized openings in the membrane,
   said metal coating having an undulated surface resembling microfolds and wrinkles when the membrane is in a relaxed state, with the wrinkles appearing to be progressively spread apart and smoothed out as the membrane is progressively stretched, thereby retaining the structural integrity of the metal coating without breaking or fracturing as the membrane is elastically stretched,
   whereby the metal coating provides an improved barrier to the passage of pathogens despite cyclically repeated stretching and relaxing of the membrane.

3. The prophylactic device of claim 2, wherein said elastic membrane comprises a member selected from the group of natural latex rubber and silicon rubber.

4. The prophylactic device of claim 2, wherein said ductile metal coating comprises aluminum that is deposited in a vapor under vacuum directly onto said elastic membrane.

5. The prophylactic device of claim 2, wherein said ductile metal coating comprises a member selected from the group of aluminum, and said elastic membrane comprises natural latex rubber and silicon rubber.

6. A multilayer flexible membrane, comprising:
a first thin continuous elastic layer having a top and a bottom surface,
a second thin continuous elastic layer having a top and a bottom surface, and
a thin continuous ductile metal layer;
wherein:
  said first and second elastic layers each respectively consist essentially of a rubber material which is capable of stretching and relaxing without normally producing a permanent set, fracture or tearing in the flexible membrane; the rubber material in the respective elastic layers consisting essentially of a matrix having submicroscopically small pores formed therein, with the pores tending to enlarge during a stretching of the flexible membrane and tending to contract during a relaxing of the flexible membrane from a stretched state;
  said top surface of the first continuous elastic layer being adjoined with said bottom surface of the second continuous elastic layer, and a stressed interface occurring at the adjoined surfaces of the two continuous elastic layers;
  said continuous ductile metal layer being adjoined to either the bottom surface of the first continuous elastic layer or the top of the second continuous elastic layer,
  the metal layer possessing an undulated or wrinkled appearance when the flexible membrane is in a relaxed state, and the undulated or wrinkled appearance of the metal layer being progressively smoothed out as the flexible membrane layer is elastically expanded, without breaking or fracturing of the metal layer.

7. A multilayer flexible membrane, comprising:
a first thin continuous elastic layer having a top and a bottom surface,
a second thin continuous elastic layer having a top and a bottom surface, and
a thin continuous ductile metal layer;
wherein:
  said first and second elastic layers each respectively consist of a rubber material capable of stretching and relaxing without normally producing a permanent set, fracture or tearing in the flexible membrane; the rubber material in the respective elastic layers consisting essentially of a matrix having submicroscopically small pores formed therein with their pores tending to enlarge during a stretching of the flexible membrane and tending to contract during a relaxing of the flexible membrane from a stretched state;
  said thin continuous ductile metal layer being sandwiched between and adjoined to the top surface of the first continuous elastic layer and the bottom surface of the second continuous elastic layer, and a stressed interface occurring between said surfaces of the first and second continuous elastic layers which adjoin the continuous ductile metal layer; and
  said flexible membrane possessing an undulated or wrinkled appearance when it is in a relaxed state, and the undulated or wrinkled appearance of the membrane being progressively smoothed out as the membrane is elastically expanded, without breaking or fracturing of the ductile metal layer therein.

8. The flexible membrane of claim 6, wherein said first and second thin elastic layers comprise silicon rubber, latex rubber, polyurethane or an elastomeric acrylic resin.

9. The flexible membrane of claim 6, wherein said first and second thin elastic layers comprise silicon rubber, latex rubber or polyurethane.

10. The flexible membrane of claim 7, wherein said first and second thin elastic layers comprise silicon rubber, latex rubber, polyurethane or an elastomeric acrylic resin.

11. The flexible membrane of claim 7, wherein said first and second thin elastic layers comprise silicon rubber, latex rubber or polyurethane.

12. A prophylactic device having an improved barrier to resist the transmission of sexually transmitted virus, including those causing AIDS and HERPES comprising:
  a hollow article having a continuous thin elastic membrane wall that is preshaped to anatomically conform to a portion of the body and provide a physical barrier resisting the transmission of pathogens,
  wherein said continuous thin elastic membrane wall comprises two elastic layers having a stressed interface therebetween,
  said elastic layers each respectively comprising a material capable of cyclical elastic stretching and relaxing without normally experiencing a permanent set or fracturing or tearing of the elastic layers,
  said material consisting essentially of a matrix having submicroscopically small pores formed therein during manufacture, with said pores tending to enlarge during stretching of the elastic layers and to contract during relaxation of the elastic layers from a stretched condition,
  a continuous thin layer of a ductile metal adjoined to an outer surface of one of the elastic layers, for sealing the pores therein,
  said ductile metal layer having an undulated or wrinkled appearance, when the membrane is in a relaxed state,
  the undulated or wrinkled appearance of the metal layer being extended and progressively smoothed out as the membrane is elastically expanded, without breaking or fracturing of the metal layer,
  whereby said metal layer improves the barrier resistance of the prophylactic member to the passage of pathogens therethrough, despite cyclically repeated elastic stretching and relaxing of the membrane.

13. The device of claim 12, wherein said thin ductile metal layer consists essentially of a continuous vacuum deposited vapor of a ductile metal.

14. The device of claim 13, wherein said ductile metal comprises aluminum.

15. The device of claim 12, wherein the material which is capable of cyclical elastic stretching is selected from the group consisting of:
  silicon rubber, latex rubber, polyurethane, and an elastomeric acrylic resin.

16. The device of claim 12, wherein the material which is capable of cyclical elastic stretching is selected from the group consisting of silicon rubber, natural latex rubber or polyurethane.

17. A prophylactic device having an improved barrier to resist the transmission of sexually transmitted virus, including those causing AIDS and HERPES comprising:
- a hollow article having a continuous thin elastic membrane wall that is preshaped to anatomically conform to a portion of the body and provide a physical barrier resisting the transmission of pathogens,
- wherein said continuous thin elastic membrane wall consists essentially of two elastic layers having a stressed interface therebetween,
- said elastic layers each respectively comprising a material which is capable of cyclical elastic stretching and relaxing without normally experiencing a permanent set or fracturing or tearing of the elastic layers,
- said material consisting essentially of a matrix having submicroscopically small pores formed therein during manufacture, with said pores tending to enlarge during stretching of the elastic layers and to contract during relaxation of the elastic layers from a stretched condition,
- a continuous thin layer of a ductile metal, sandwiched between and adjoining each of the elastic layers for sealing the pores therein,
- said elastic membrane wall having an undulated or wrinkled appearance, when the membrane wall is in a relaxed state,
- the undulated or wrinkled appearance being extended and progressively smoothed out as the membrane wall is elastically expanded, without breaking or fracturing of the metal layer,
- whereby said metal layer improves the barrier resistance of the prophylactic member to the passage of pathogens therethrough, despite cyclically repeated elastic stretching and relaxing of the membrane.

18. The device of claim 17, wherein said thin ductile metal layer consists essentially of a continuous vacuum deposited vapor of a ductile metal.

19. The device of claim 18, wherein said ductile metal comprises aluminum.

20. The device of claim 17, wherein the material which is capable of cyclical elastic stretching is selected from the group consisting of:
silicon rubber, latex rubber, polyurethane, and an elastomeric acrylic resin.

21. The device of claim 17, wherein the material which is capable of cyclical elastic stretching is selected from the group consisting of silicon rubber, natural latex rubber or polyurethane.

22. A prophylactic device having improved barrier resistance to the passage of pathogens, including the virus causing AIDS, comprising:
the multilayer flexible membrane recited in claim 6.

23. A prophylactic device having improved barrier resistance to the passage of pathogens, including the virus causing AIDS, comprising: the multilayer flexible membrane recited in claim 8.

24. A prophylactic device having improved barrier resistance to the passage of pathogens, including the virus causing AIDS, comprising:
the multilayer flexible membrane recited in claim 9.

25. A prophylactic device having improved barrier resistance to the passage of pathogens, including the virus causing AIDS, comprising:
the multilayer flexible membrane recited in claim 7.

26. A prophylactic device having improved barrier resistance to the passage of pathogens, including the virus causing AIDS, comprising:
the multilayer flexible membrane recited i claim 10.

27. A prophylactic device having improved barrier resistance to the passage of pathogens, including the virus causing AIDS, comprising:
the multilayer flexible membrane recited in claim 11.

28. The prophylactic device of claim 22, wherein the ductile metal layer of the multilayer flexible membrane comprises aluminum.

29. The prophylactic device of claim 25, wherein the ductile metal layer of the multilayer flexible membrane comprises aluminum.

30. A flexible electrode, comprising: the multilayer flexible membrane recited in claim 6.

31. A flexible electrode, comprising: the multilayer flexible membrane recited in claim 8.

32. A flexible electrode, comprising: the multilayer flexible membrane recited in claim 9.

33. A flexible electrode, comprising: the multilayer flexible membrane recited in claim 7.

34. A flexible electrode, comprising: the multilayer flexible membrane recited in claim 10.

35. A flexible electrode, comprising: the multilayer flexible membrane recited in claim 11.

36. A flexible electrode as recited in claim 30, wherein the ductile metal layer of the multilayer flexible membrane comprises a nobel metal.

37. A flexible electrode as recited in claim 33, wherein the ductile metal layer of the multilayer flexible membrane comprises a nobel metal.

38. A flexible electrode comprising:
(a) a first continuous thin elastic membrane layer; and
(b) a thin layer of a ductile metal, which is on an outer surface of said membrane layer, said membrane layer comprising a first material which is capable of stretching and relaxing without normally experiencing a permanent set or fracturing or tearing of the membrane layer, and said first material consisting essentially of a matrix having submicroscopically small pores formed therein during manufacture, with said pores tending to enlarge during stretching of the membrane and to contract during relaxation of the membrane from a stretched state;
(c) a second thin continuous elastic membrane layer adjoined to said ductile metal layer, said second membrane layer comprising a second material which is capable of stretching and relaxing without normally experiencing a permanent set or fracturing or tearing of the membrane layer, and said second material consisting of a matrix having submicroscopically small pores formed therein during manufacture, with said pores tending to enlarge during stretching of the membrane and to contract during relaxation of the membrane from a stretched state,
with the proviso that at least a portion of said ductile metal layer is exposed; and
said ductile metal layer having an undulating surface when the membrane is in a relaxed state, and said undulating surface being extended and progressively smoothed out as the membrane layer is elastically expanded, without breaking or fracturing of the ductile metal layer.

39. The flexible electrode of claim 38, further comprising an electrical contact lead that is in contact with said ductile metal layer.

40. A flexible electrode comprising:
(a) a first continuous thin elastic membrane layer; and
(b) a thin layer of a ductile metal, which is on an outer surface of said membrane layer, said membrane layer comprising a first material which is capable of stretching and relaxing without normally experiencing a permanent set or fracturing or tearing of the membrane layer, and said first material consisting essentially of a matrix having submicroscopically small pores formed therein during manufacture, with said pores tending to enlarge during stretching of the membrane and to contract during relaxation of the membrane from a stretched state; and
(c) an electrical contact lead that is in contact with said ductile metal layer;
said ductile metal layer having an undulating surface when the membrane is in a relaxed state, and said undulating surface being extended and progressively smoothed out as the membrane layer is elastically expanded, without breaking or fracturing of the ductile metal layer.

* * * * *